(12) United States Patent
Goodman

(10) Patent No.: US 11,540,856 B2
(45) Date of Patent: Jan. 3, 2023

(54) METHODS AND SYSTEMS FOR ULTRASONIC VESSEL SEALING

(71) Applicant: COVIDIEN LP, Mansfield, MA (US)

(72) Inventor: Kelly E. Goodman, Boulder, CO (US)

(73) Assignee: Covidien LP, Mansfield, MA (US)

(*) Notice: Subject to any disclaimer, the term of this patent is extended or adjusted under 35 U.S.C. 154(b) by 466 days.

(21) Appl. No.: 16/391,635

(22) Filed: Apr. 23, 2019

(65) Prior Publication Data
US 2019/0365410 A1 Dec. 5, 2019

Related U.S. Application Data

(60) Provisional application No. 62/678,724, filed on May 31, 2018.

(51) Int. Cl.
*A61B 17/32* (2006.01)
*A61B 17/00* (2006.01)

(52) U.S. Cl.
CPC ........ *A61B 17/320092* (2013.01); *A61B 2017/00039* (2013.01); *A61B 2017/00119* (2013.01);
(Continued)

(58) Field of Classification Search
CPC ......... A61B 17/320092; A61B 2017/320095; A61B 2017/00039; A61B 2017/00119;
(Continued)

(56) References Cited

U.S. PATENT DOCUMENTS

| 4,750,488 A | 6/1988 | Wuchinich et al. |
| 5,722,403 A * | 3/1998 | McGee .............. A61N 1/056 600/373 |

(Continued)

FOREIGN PATENT DOCUMENTS

| CN | 101330874 A | 12/2008 |
| CN | 104582606 A | 4/2015 |

(Continued)

OTHER PUBLICATIONS

Notice of Reasons for Rejection issued by the Japanese Patent Office dated Apr. 1, 2020 in corresponding Japanese Patent Application No. 2019-093560, with English translation.

(Continued)

*Primary Examiner* — Linda C Dvorak
*Assistant Examiner* — Lindsay Regan Lancaster
(74) *Attorney, Agent, or Firm* — Carter, DeLuca & Farrell LLP

(57) ABSTRACT

A method includes providing electrical energy to a transducer for sealing a vessel, where a frequency of the electrical energy is in an ultrasound range, controlling the electrical energy to achieve a predetermined velocity of an end effector coupled to the transducer, when the end effector is grasping the vessel, sensing parameters of the electrical energy when the end effector achieves the predetermined velocity, calculating power of the electrical energy based on the sensed parameters and estimating a size range of the vessel based on the power, and controlling the electrical energy to achieve a target velocity, which is determined based on the estimated size range of the vessel, to seal the vessel.

20 Claims, 4 Drawing Sheets

(52) U.S. Cl.
CPC ........... *A61B 2017/00402* (2013.01); *A61B 2017/00778* (2013.01); *A61B 2017/320095* (2017.08)

(58) Field of Classification Search
CPC ........... A61B 2017/00402; A61B 2017/00778; A61B 2017/00075; A61B 17/320068; A61B 2017/320072
See application file for complete search history.

(56) References Cited

U.S. PATENT DOCUMENTS

| | | | |
|---|---|---|---|
| 6,259,078 B1* | 7/2001 | Araya | F26B 3/347 |
| | | | 219/709 |
| 9,439,669 B2 | 9/2016 | Wiener et al. | |
| 9,445,832 B2 | 9/2016 | Wiener et al. | |
| 9,498,245 B2 | 11/2016 | Voegele et al. | |
| 9,504,855 B2 | 11/2016 | Messerly et al. | |
| 9,623,237 B2 | 4/2017 | Turner et al. | |
| 9,642,644 B2 | 5/2017 | Houser et al. | |
| 9,649,126 B2 | 5/2017 | Robertson et al. | |
| 9,687,236 B2 | 6/2017 | Leimbach et al. | |
| 9,690,362 B2 | 6/2017 | Leimbach et al. | |
| 9,700,343 B2 | 7/2017 | Messerly et al. | |
| 9,724,120 B2 | 8/2017 | Faller et al. | |
| 9,730,695 B2 | 8/2017 | Leimbach et al. | |
| 9,733,663 B2 | 8/2017 | Leimbach et al. | |
| 2005/0107750 A1 | 5/2005 | Barongan | |
| 2005/0192612 A1* | 9/2005 | Houser | A61B 17/12 |
| | | | 606/169 |
| 2011/0092972 A1* | 4/2011 | Allen | A61B 17/320092 |
| | | | 606/45 |
| 2011/0213397 A1 | 9/2011 | Mathonnet | |
| 2011/0257650 A1 | 10/2011 | Deville et al. | |
| 2012/0071796 A1* | 3/2012 | Smith | A61B 17/320092 |
| | | | 601/3 |
| 2013/0030328 A1* | 1/2013 | Dycus | A61B 17/320092 |
| | | | 601/2 |
| 2013/0289592 A1 | 10/2013 | Stulen et al. | |
| 2014/0277029 A1 | 9/2014 | Messerly et al. | |
| 2015/0196349 A1* | 7/2015 | Wham | A61B 18/1206 |
| | | | 606/34 |
| 2016/0023021 A1* | 1/2016 | Liu | B06B 1/0261 |
| | | | 606/27 |
| 2017/0000553 A1* | 1/2017 | Wiener | A61B 18/1233 |
| 2017/0296169 A1* | 10/2017 | Yates | A61B 17/068 |
| 2018/0069394 A1* | 3/2018 | Hagen | G01R 21/06 |
| 2018/0146976 A1* | 5/2018 | Clauda | A61B 17/320092 |

FOREIGN PATENT DOCUMENTS

| | | |
|---|---|---|
| CN | 107928784 A | 4/2018 |
| JP | 2006051445 A | 2/2006 |
| JP | 3911368 B2 | 5/2007 |
| WO | 0134018 A2 | 5/2001 |
| WO | 2017003852 A1 | 1/2017 |
| WO | 2017003853 A1 | 1/2017 |
| WO | 2017141324 A1 | 8/2017 |
| WO | 2017187530 A1 | 11/2017 |

OTHER PUBLICATIONS

Examination Report issued by the Australian Intellectual Property Office dated Jun. 26, 2019 in corresponding Australian Patent Application No. 2019203019.

Notice for Reasosn for Rejection issued in corresponding Japanese Appl. No. 2019-093560 dated Dec. 25, 2020 (2 pages), together with English language translation (4 pages).

Extended European Search Report issued by the European Patent Office in corresponding European Patent Application No. 19177480.1 dated Jul. 31, 2019.

Chinese Office Action issued in corresponding Chinese Application No. 201910465790.3 dated Feb. 14, 2022.

* cited by examiner

METHODS AND SYSTEMS FOR ULTRASONIC VESSEL SEALING

CROSS REFERENCE TO RELATED APPLICATION

The present application claims the benefit of and priority to U.S. Provisional Application Ser. No. 62/678,724, filed on May 31, 2018 the entire contents of which are incorporated herein by reference.

BACKGROUND

Technical Field

The present disclosure relates to an ultrasonic surgical device for sealing a vessel. More particularly, the present disclosure relates to an ultrasonic surgical device that automatically estimates a size range of the vessel and controls electrical energy to seal the vessel.

Background of Related Art

Ultrasonic surgical devices have been demonstrated to provide outstanding hemostasis and efficient sealing of tissue with minimum lateral thermal damage and low smoke generation. Unlike electrosurgical devices, which require electrical current to flow through a patient, ultrasonic surgical devices operate by applying mechanical action of a transducer that is driven at a mechanical resonant frequency.

Vessels are different in size range and thus sealing of vessels benefits from different velocity of an end effector, which is mechanically coupled to the transducer. If higher velocity is exerted to a smaller vessel, the vessel may burst, and if lower velocity is exerted to a bigger vessel, the vessel may not be adequately sealed. Accordingly, there is continuing interest in improving vessel sealing to account for properties of the target vessel.

SUMMARY

The present disclosure provides an ultrasonic surgical device for estimating a size range of vessel prior to sealing the vessel, and a method for controlling such ultrasonic surgical device. By maintaining an appropriate velocity of an end effector of the ultrasonic surgical device based on the estimated size range of the vessel, the ultrasonic surgical device is capable of more adequately sealing the vessel.

In accordance with aspects of the present disclosure, the present disclosure includes a method for controlling an ultrasonic surgical device. The method includes providing electrical energy to a transducer for sealing a vessel, where a frequency of the electrical energy is in an ultrasound range, controlling the electrical energy to achieve a predetermined velocity of an end effector coupled to the transducer, when the end effector is grasping the vessel, sensing parameters of the electrical energy when the end effector achieves the predetermined velocity, calculating power of the electrical energy based on the sensed parameters and estimating a size range of the vessel based on the power, and controlling the electrical energy to achieve a target velocity, which is determined based on the estimated size range of the vessel, to seal the vessel.

In various embodiments, the size range of the vessel is greater than or equal to 5 millimeters (mm) when the power is greater than or equal to a predetermined power threshold.

In various embodiments, the size range of the vessel is less than 5 mm when the power is less than a predetermined power threshold.

In various embodiments, controlling the electrical energy based on the estimated size range of the vessel includes controlling power of the electrical energy to seal the vessel based on the estimated size range of the vessel.

In various embodiments, the power is calculated by subtracting power losses in the transducer and a waveguide in the ultrasonic surgical device from the power of the electrical energy.

In various embodiments, the power is calculated about 100 milliseconds after providing the electrical energy.

In various embodiments, controlling the electrical energy based on the estimated size range of the vessel to seal the vessel includes determining whether the power is in a first range or in a second range, which is at least partially higher than the first range, and setting a first target velocity when the power is determined to be in the first range, and a second target velocity when the power is determined to be in the second range. Controlling the electrical energy based on the estimated size range of the vessel to seal the vessel includes controlling the electrical energy to maintain the first or second target velocity of the end effector to seal the vessel. The first target velocity is greater than the predetermined velocity. The second target velocity is less than the predetermined velocity.

In accordance with aspects of the present disclosure, the present disclosure includes an ultrasonic surgical device including a transducer, an end effector coupled to the transducer and configured to grasp and seal a vessel, a power source configured to supply electrical energy to the transducer, a sensor configured to sense parameters of the electrical energy, a controller configured to achieve a predetermined velocity of an end effector coupled to the transducer, when the end effector is grasping the vessel, calculate power of the electrical energy based on the sensed parameters, estimate a size range of the vessel based on the power, and control the electrical energy to achieve a target velocity, which is determined based on the estimated size range of the vessel, to seal the vessel.

In various embodiments, the size range of the vessel is greater than or equal to 5 mm when the power is greater than or equal to a predetermined power threshold.

In various embodiments, the size range of the vessel is less than 5 mm when the power is less than a predetermined power threshold.

In various embodiments, the controller is further configured to control power of the electrical energy to seal the vessel based on the estimated size range of the vessel.

In various embodiments, the power is calculated by subtracting power losses in the transducer and a waveguide in the ultrasonic surgical device from the power of the electrical energy.

In various embodiments, the power is calculated about 100 milliseconds after providing the electrical energy.

In various embodiments, the controller is further configured to determine whether the power is in a first range or in a second range, which is at least partially higher than the first range and set a first target velocity when the power is determined to be in the first range, and a second target velocity when the power is determined to be in the second range. The controller is further configured to control the electrical energy to maintain the first or second target velocity of the end effector to seal the vessel. The first target velocity is greater than the predetermined velocity. The second target velocity is less than the predetermined velocity.

Further details and aspects of exemplary embodiments of the present disclosure are described in more detail below with reference to the appended figures.

BRIEF DESCRIPTION OF THE DRAWINGS

The present disclosure may be understood by reference to the accompanying drawings, when considered in conjunction with the subsequent, detailed description, in which.

DETAILED DESCRIPTION

Generally, the present disclosure provides an ultrasonic surgical device for sealing a vessel in tissue and a method for controlling the ultrasonic surgical device. An ultrasonic surgical device utilizes a transducer to generate ultrasonic mechanical motions. In accordance with aspects of the present disclosure, the ultrasonic surgical device automatically estimates a size range of a vessel to be sealed prior to sealing the vessel. Based on the estimated size range of the vessel, the ultrasonic surgical device maintains an appropriate velocity of an end effector to adequately seal the vessel.

In accordance with the present disclosure, an ultrasonic surgical device includes various controls, which may be embodied in hardware and/or software executed by a processor, to control the ultrasonic mechanical motion of the transducer, which is energized by a DC power source. One control is an amplitude control to regulate the longitudinal mode displacement of the end effector. Another control generates an AC signal from the DC power and tracks the resonant frequency of the transducer. By using the various controls, the ultrasonic surgical device provides controlled ultrasonic mechanical motions sufficient to treat the vessel in accordance with embodiments of the present disclosure.

Since different vessels benefit from different velocity of the end effector to adequately treat the vessels, the ultrasonic surgical device estimates a size range of the vessel prior to treating the vessel. Based on the estimated size range of the vessel, the ultrasonic surgical device sets a velocity of the end effector to adequately treat the vessel.

Figure 1A:
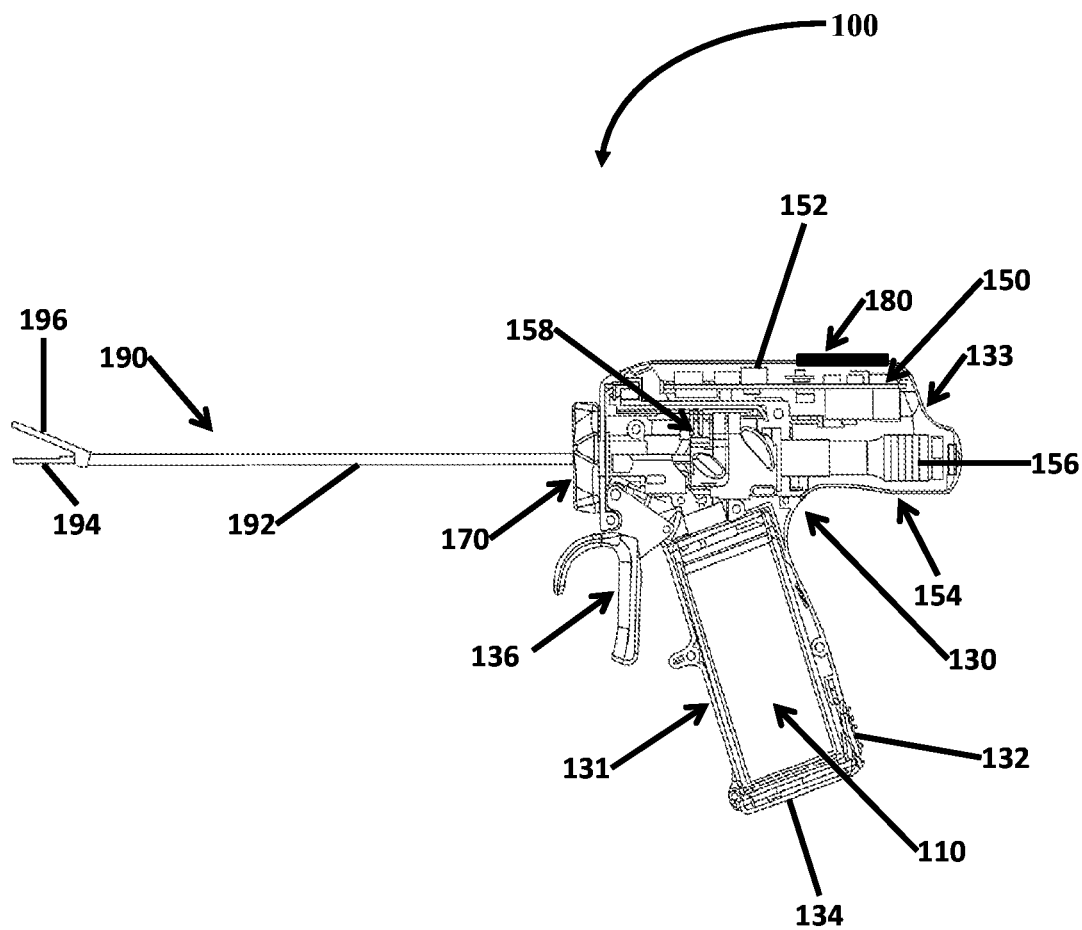
FIG. 1A is a side elevation view of an ultrasonic surgical device in accordance with embodiments of the present disclosure.
Figure 1B:
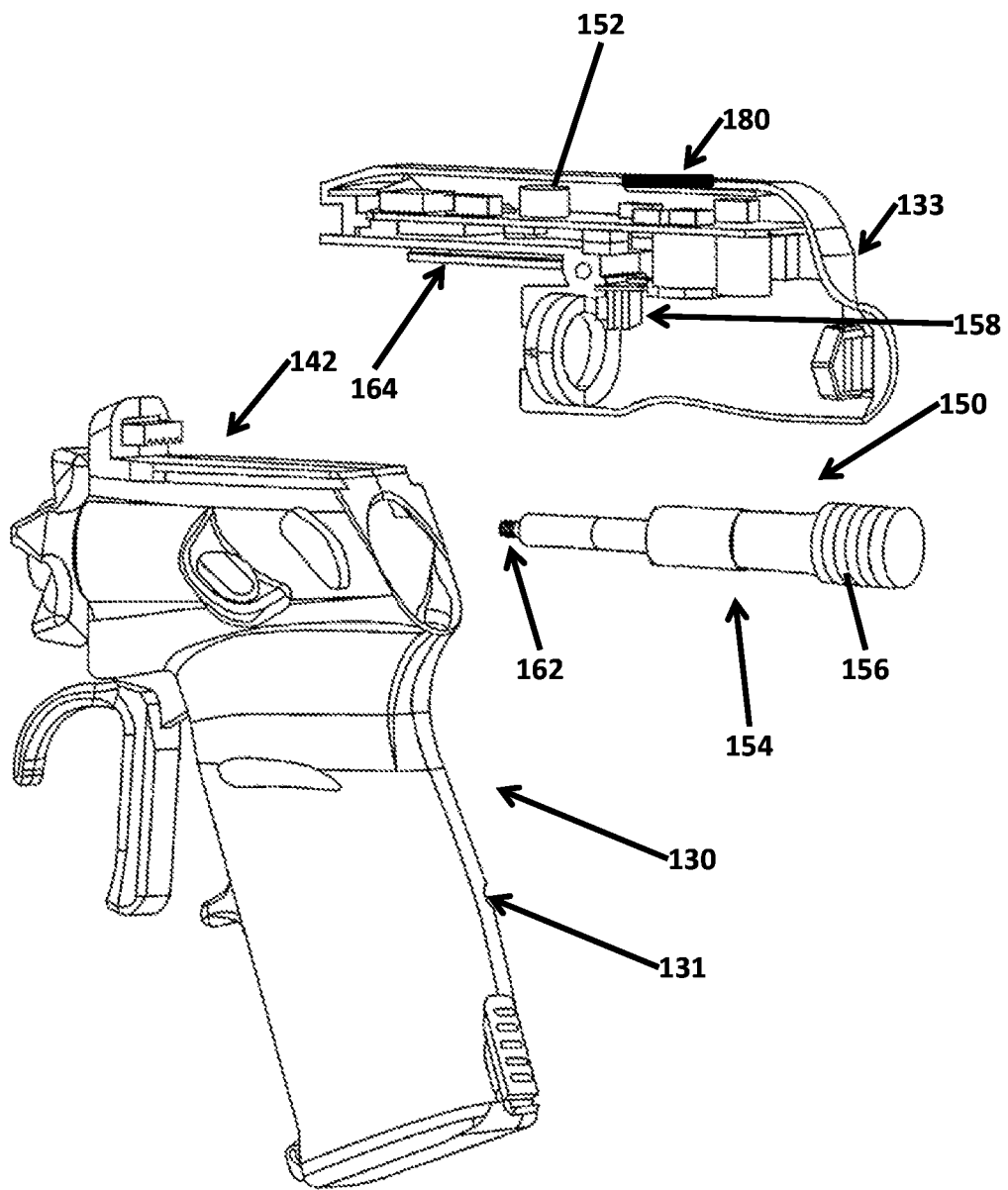
FIG. 1B is a perspective view of parts separated, which shows the left portion of a handle, a transducer, and the right portion of the ultrasonic surgical device of FIG. 1A in accordance with embodiments of the present disclosure.

With reference to FIGS. 1A and 1B, an ultrasonic surgical device 100 for treating tissue is illustrated. The ultrasonic surgical device 100 includes a power source 110, a housing 130, a transducer 150, and an ultrasonic probe 190. The power source 110 provides DC power to the transducer 150. In an embodiment, the power source 110 may be a portable power source, such as a battery, that can be carried to provide DC power at any place. In a further embodiment, the power source 110 may be insertable or integrated into the housing 130 so that the ultrasonic surgical device 100 may be portably carried without disturbances of any cable. In yet another embodiment, the power source 110 may be rechargeable so that the power source 110 may be reusable. In yet another embodiment, the power source 110 may receive power from a wall outlet.

In another embodiment, the power source 110 may include a converter that is connected to an alternating current (AC) power source and converts the AC power to DC power. The AC power source may be of a relatively low frequency, such as about 60 hertz (Hz), while the ultrasonic surgical device 100 operates at a higher frequency. Thus, the power source 110 may convert the low frequency AC power to DC power so that the DC power may then be inverted to AC power having a frequency suitable to cause the transducer 150 to generate ultrasonic mechanical motions.

With continued reference to FIGS. 1A and 1B, the housing 130 includes a handle portion 131 having a compartment 132, which may house the power source 110, and a power source door 134 that secures the power source 110 within the compartment 132. In an aspect, the power source door 134 may be configured to form a water-tight seal between the interior and the exterior of the compartment 132.

The housing 130 also includes a cover 133, which houses the transducer 150 and an output device 180. The transducer 150 includes a generator assembly 152 and a transducer assembly 154, having a transducer body 156 and a locking portion 162 (FIG. 1B). The generator assembly 152 is electrically coupled to the transducer assembly 154 via a pair of contacts 158.

With reference to FIG. 1B, the transducer 150 is illustrated as being separate from the cover 133. When the transducer 150 is inserted into and assembled with the cover 133, the pair of contacts 158 is connected to the round groove of the transducer 150 so that the rotational movement of the transducer body 156 does not disrupt the connection between the transducer body 156 and the generator assembly 152. Thus, the transducer body 156 is capable of freely rotating within the housing 130.

The output device 180 outputs information about the ultrasonic surgical device 100 or, in various embodiments, a status of the mechanical coupling between the ultrasonic probe 190 and the transducer 150. In various embodiments, the output device 180 may also display a warning that the ultrasonic probe 190 is not adequately connected to the transducer 150.

In another embodiment, the output device 180 may be a speaker configured to output audible tones denoting a proper or improper connection of the ultrasonic probe 190 to the transducer 150. In yet another embodiment, the output device 180 may include one or more light emitting devices, configured to emit lights of various duration, pulses, and colors indicating the status of the mechanical coupling between the ultrasonic probe 190 and the transducer 150.

The handle portion 131 further includes a trigger 136. When the trigger 136 is actuated, the power source 110 provides energy to the transducer 150 so that the transducer 150 is powered to generate ultrasonic mechanical motion of the ultrasonic probe 190. As the trigger 136 is released, the power supply to the transducer 150 is terminated.

The generator assembly 152 receives the DC power from the power source 110 and generates AC signals having a frequency greater than 20 kHz. The generator assembly 152 may be capable of generating signals having a frequency based on a desired mode of operation, which may be different from the resonant frequency of the transducer 150.

The transducer body 156 of the transducer assembly 154 receives the AC signal generated by the generator assembly 152 and generates ultrasonic mechanical motion within the ultrasonic probe 190 based on the amplitude and the frequency of the generated AC signal. The transducer body 156 includes a piezoelectric material, which converts the generated AC signal into ultrasonic mechanical motions.

The ultrasonic surgical device 100 also includes a spindle 170, which is coupled to the ultrasonic probe 190 and allows for rotation of the ultrasonic probe 190 about its longitudinal axis. The ultrasonic probe 190 is attached to the housing and is mechanically connected to the transducer 150 via the locking portion 162 such that as the spindle 170 is rotated about the longitudinal axis defined by the ultrasonic probe 190, the ultrasonic probe 190 and the transducer 150 are also rotated correspondingly without affecting the connection between the transducer 150 and the ultrasonic probe 190.

The ultrasonic probe 190 may include an end effector suitable for sealing tissue. The ultrasonic probe 190 includes a waveguide 192, an end effector 194 extending from the waveguide 192, and a jaw member 196. The ultrasonic probe 190 is mechanically coupled to the transducer body 156 via the locking portion 162.

The jaw member 196 may be formed as a pivoting arm configured to grasp and/or clamp tissue between the jaw member 196 and the end effector 194. When the jaw member 196 and the end effector 194 grasp tissue and the end effector 194 conveys the ultrasonic mechanical motions, temperature of the grasped tissue between the end effector 194 and the jaw member 196 increases due to the ultrasonic mechanical motions. These motions in turn treat, e.g., cuts and/or seals, a vessel in the tissue. In an aspect, the end effector 194 may vibrate at a different velocity based on a size range of a vessel to be sealed.

The illustrated embodiments of FIG. 1A and FIG. 1B are merely exemplary, and variations are contemplated to be within the scope of the present disclosure. For example, components need not be arranged or configured as illustrated in FIG. 1A and FIG. 1B, and may be arranged or configured in a different way while still performing the operations and/or functions described herein.

Figure 2:
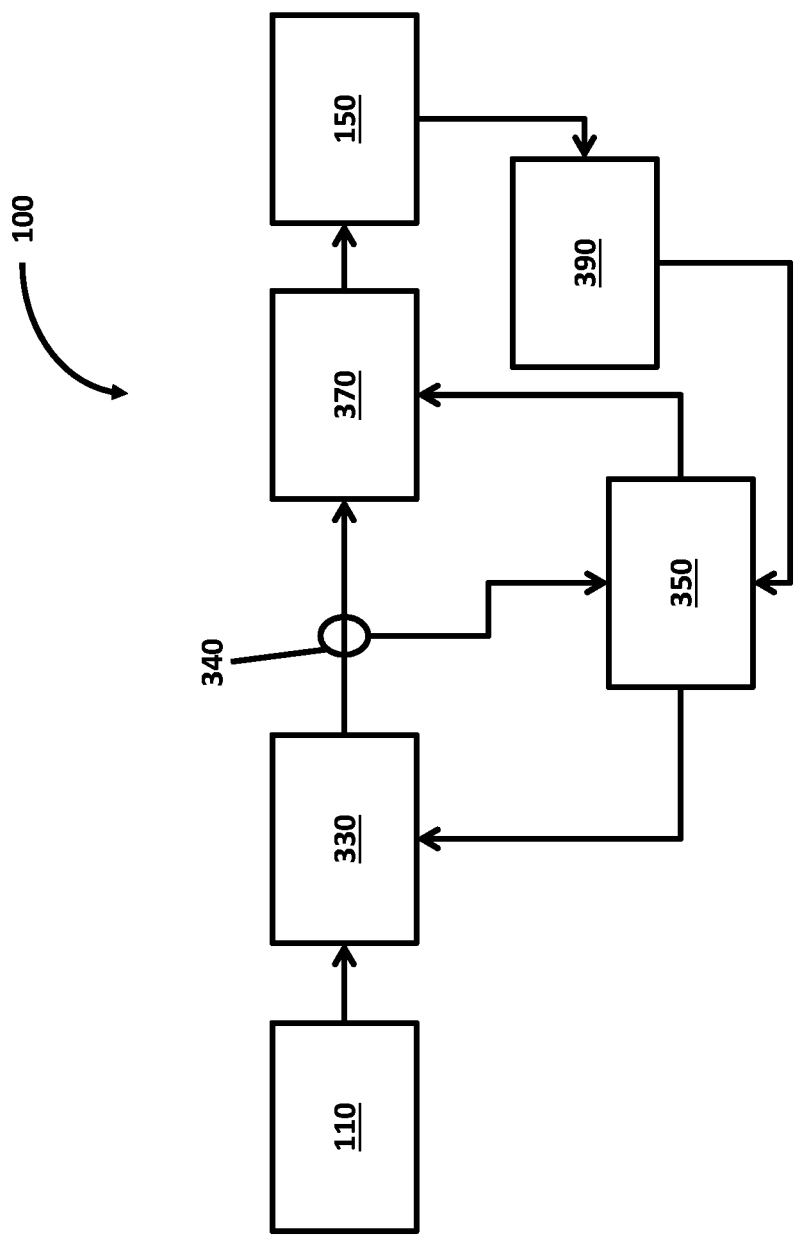
FIG. 2 is a functional block diagram of the ultrasonic surgical device of FIG. 1A in accordance with embodiments of the present disclosure.

FIG. 2 illustrates a functional block diagram of the ultrasonic surgical device 100 of FIG. 1. As described above, the ultrasonic surgical device 100 estimates a size range of a vessel to be sealed and provides electrical energy, which has a suitable power and frequency, to the transducer 150, which in turn provides ultrasonic mechanical motions to the end effector 192. An analog or digital pulse-width modulation (PWM) signal may be used to regulate the ultrasonic mechanical motions. The ultrasonic surgical device 100 includes the power source 110, a converter 330, a sensor 340, a controller 350, an inverter 370, the transducer 150, and a comparator 390.

The power source 110 provides DC power to the converter 330, which amplifies the amplitude of the DC power so that ultrasonic surgical device 100 generates ultrasonic mechanical motions sufficiently large enough for treating the tissue. The sensor 340 then senses parameters related to the electrical energy flowing to the inverter 370. The sensed parameters may include sensed current waveforms and the sensed voltage waveforms of the electrical energy supplied to the inverter 370.

The controller 350 receives the sensed parameters from the sensor 340, calculates various parameters (e.g., root-mean-square (RMS) or average voltage, current, power or impedance) based on the sensed parameters, and generates a control signal to control a duty cycle of the converter 330. In an embodiment, a digital PWM signal may be used to control the duty cycle of the converter 330.

The inverter 370 receives the amplified DC signals from the converter 330. The inverter 370 is driven by output signals from the controller 350. In various embodiments, the inverter 370 may include an H-bridge structure to generate the electrical energy having a suitable frequency to cause the transducer 150 to mechanically vibrate.

In various embodiments, the controller 350 may measure a velocity of the end effector 194 coupled to the transducer 150 and maintain a certain velocity of the end effector 194 during a sealing process. The comparator 390 receives a signal from the transducer 150, indicating a velocity of the end effector 194, and compares the velocity of the end effector 194 with a pre-determined velocity set for estimating a size range of vessel. If the velocity is less than the pre-determined velocity, the controller 350 may generate a control signal to increase the amplitude of the electrical energy to cause the transducer 150 vibrate farther resulting in increase in the velocity of the end effector 194. If the velocity is greater than the predetermined velocity, the controller 350 may generate another control signal to decrease the amplitude of the electrical energy so as to cause the transducer 150 vibrate less, resulting in decrease in the velocity.

When the velocity of the end effector 194 has achieved the pre-determined velocity threshold, the controller may then estimate a size range of the vessel to be treated. In particular, the controller 350 calculates the power of the electrical energy and estimates the size range of the vessel to be treated based on the power. In one embodiment, if the power is less than a pre-determined threshold power, the size range of the vessel is estimated to be less than 5 mm or a small vessel, and if the power is greater than or equal to the pre-determined threshold power, the size range of the vessel is estimated to be greater than 5 mm or the vessel is large.

When supply of the electrical energy is started, time is needed for the velocity of the end effector to achieve the predetermined velocity. Thus, a time period may be utilized to allow the velocity to achieve the predetermined velocity. In an aspect, a time period of 100 milliseconds (ms) may pass prior to measurements or calculations after supply of the electrical energy has been started. However, this time period prior to measurements or calculations is not limited to 100 ms and can be less or greater than 100 ms.

The controller 350 may generate PWM control signals to drive the converter 330 and other control signals for the inverter 370. The controller 350 receives outputs from the comparator 390 and generates control signals for the inverter 370 in response to the output of the comparator 390. The inverter 370 then inverts the DC power to the AC signal. In an aspect, a transformer (not shown) may be electrically coupled between the inverter 370 and the transducer 150 so that the transformer may increase or decrease the amplitude of the inverted AC power to a desired level.

In an aspect, the sensor 340 is configured to sense voltage and current waveforms of the broadband AC signals supplied to the transducer 150 and transmit the sensor signals to the controller 350. The controller 350 may process the sensor signals and the output of the comparator 390 to control the velocity of the end effector 194.

Figure 3:
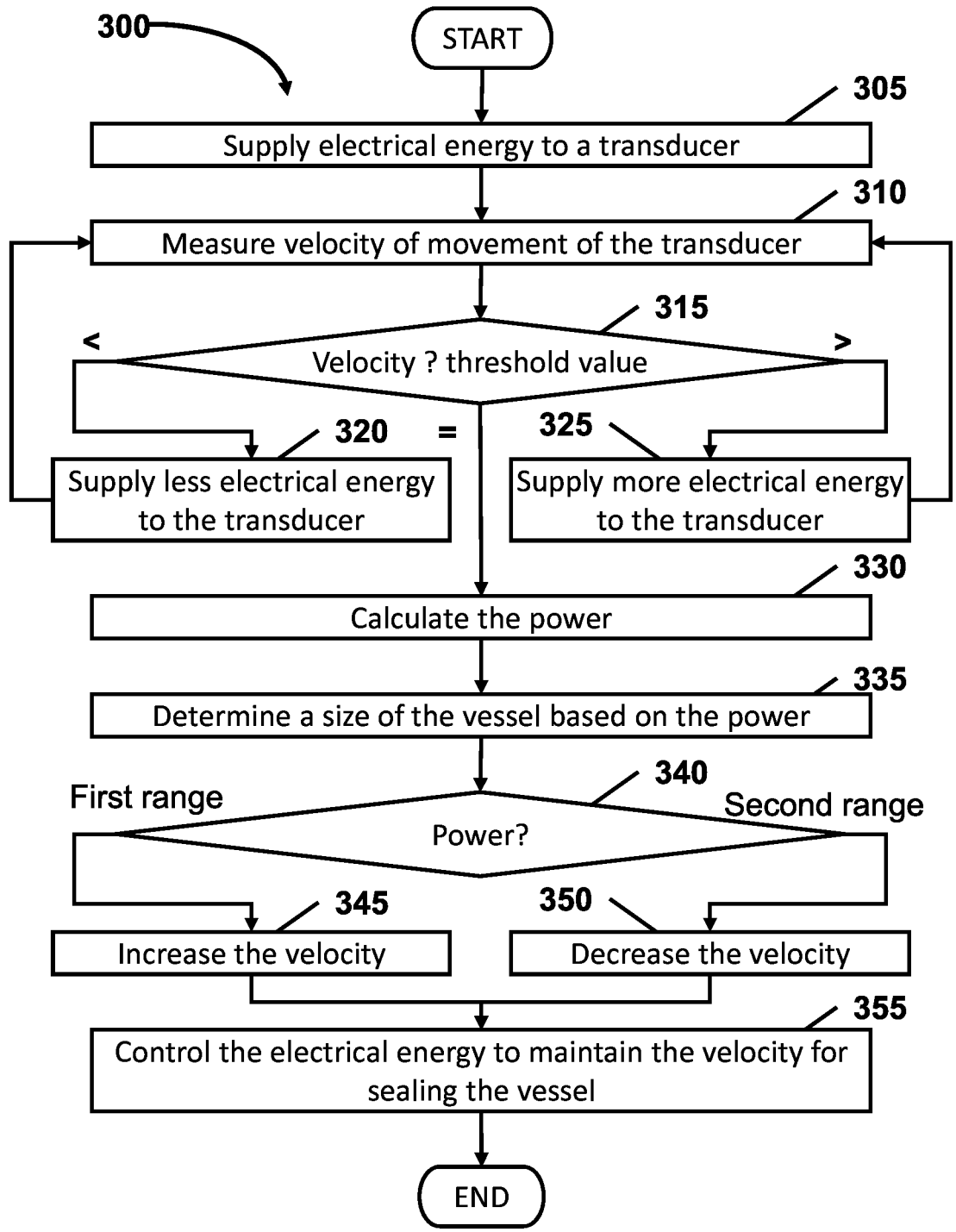
FIG. 3 is a flow chart illustrating a method for controlling an ultrasonic surgical device in accordance with embodiments of the present disclosure.

In an aspect, the controller 350 may include a processor and a memory coupled to the processor. The processor may be any suitable processor (e.g., control circuit) adapted to perform operations, calculations, and/or set of instructions described in the present disclosure including, but not limited to, a hardware processor, a field programmable gate array (FPGA), a digital signal processor (DSP), a central processing unit (CPU), a microprocessor, and any combinations thereof. Those skilled in the art will appreciate that the processor may be substituted for by using any logic processor (e.g., control circuit) adapted to execute algorithms, calculations, and/or set of instructions described in this disclosure. The memory may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory FIG. 3 shows a flow chart illustrating a method 300 for controlling an ultrasonic transducer to adequately seal vessel. The method 300 includes two phases, one of which achieves a predetermined velocity at the end effector and another which determines a size range of the vessel to be sealed and sets a velocity of an end effector accordingly.

When an end effector coupled to a transducer grabs tissue including a vessel, the first control of the method 300 starts with supplying electrical energy to the transducer in step 305. The electrical energy includes a frequency and amplitude, which control a velocity of the end effector mechanically coupled to the transducer. The mechanical motions of the transducer are measured and a velocity of movements of the end effector is calculated in step 310.

Since bigger size range vessels typically require more electrical energy to maintain a velocity, the measured velocity is compared with a threshold velocity in step 315. When it is determined that the velocity of the end effector is less than the threshold velocity, more electrical energy is supplied to the transducer in step 320. When it is determined that the velocity of the end effector is greater than the threshold velocity, less electrical energy is supplied to the transducer in step 325. In this manner, the velocity of the end effector is controlled to achieve the predetermined velocity.

When the velocity is determined to have achieved the threshold velocity in step 315, the power of the supplied electrical energy is calculated in step 330. In an aspect, since the velocity of the end effector may take time to achieve the predetermined velocity, the comparisons in step 315 may be performed a certain time period after the end effector is actuated. For example, the predetermined period may be 100 ms.

In an aspect, the power may be calculated from the sensed results. For example, the power may be calculated by multiplying the voltage waveform and the current waveform. In another aspect, the power may be calibrated so as to calculate a power actually applied to the tissue. This calculation may be performed by subtracting power losses in the waveguide and in the transducer from the result obtained by multiplying the voltage waveform and the current waveform. Further, the predetermined power threshold may also be set based on a type of tissue including the vessel to be treated.

In various embodiments, the power loss in the transducer may be based on variability in properties of the piezo electric stacks of the transducer. Power calibration process may involve open jaw activations to determine scaling factors for voltage, current, velocity, and frequency measurements and may include measuring the power drawn for the open jaw activation. In embodiments, the calibration parameters related to the transducer may be stored in a memory so as to be used for a later power calibration process.

In various embodiments, the power losses in the waveguide and in the transducer can be calibrated values that are stored in a memory of the ultrasonic device. The waveguide may vary in length, resulting in different power loss therein. Parameters related to the power loss based on the length of the waveguide may be stored in a memory and can be read from the memory to calibrate the power loss while estimating the size range and performing vessel sealing.

Based on the calculated power, the size range of the vessel may be determined in step 335. For example, if the calculated power is lower than a predetermined power threshold, the vessel is determined to be a small vessel, which is smaller than 5 mm. If the calculated power is greater than or equal to the predetermined power threshold, the vessel is determined to be a large vessel, which is greater than or equal to 5 mm and less than 7 mm.

In an aspect, the predetermined power threshold may be differently set based on a type of vessel. For example, the predetermined power threshold for a renal artery may be different from that for a carotid artery or a femoral artery.

The calculated power is then compared with two ranges in step 340 to set a target velocity of the end effector to adequately seal the vessel. When the calculated power falls in a first range or the vessel is determined to be a small vessel, the target velocity is set so as to be larger than the predetermined velocity in step 345. For example, if the calculated power is in between 18 watts (W) and 23.5 W, then the target velocity is increased.

When the calculated power falls in a second range, which is higher than the first range, or the vessel is determined to be a large vessel, the target velocity is set so as to be smaller than the predetermined velocity in step 350. For example, if the calculated power is in between 26.5 W and 36 W, the target velocity is decreased. The values of the first and second ranges are provided merely as examples, and the first and second ranges are not limited to these values and may have different values.

In step 355, the electrical energy is controlled so as to maintain the velocity of the end effector at the target velocity. The vessel is then adequately sealed at the target velocity and the method 300 is ended. In an aspect, the duration of the sealing process may be controlled depending on the size range of the vessel. In other words, the small vessel may be sealed faster than the large vessel.

In various embodiments, step 315 may not proceed to step 330 when the velocity achieves a predetermined velocity threshold. Rather, in various embodiments, step 315 may proceed to step 330 only after a certain time period has elapsed, such as 100 ms.

In various embodiments, step 345 may not merely increase the target velocity and step 350 may not merely decrease the target velocity. In various embodiments, step 345 may access a first velocity curve, and step 350 may access a second velocity curve. As used herein, a velocity curve is a function, table, or other numerical relationship that specifies velocity over time. Then, step 355 would control the electrical energy so that the velocity of the end effector tracks the particular velocity curve over time.

Since other modifications and changes may be made to fit particular operating requirements and environments, it is to be understood by one skilled in the art that the present disclosure is not limited to the illustrative examples described herein and may cover various other changes and modifications which do not depart from the spirit or scope of this disclosure.

What is claimed is:

1. A method for controlling an ultrasonic surgical device, the method comprising:
providing electrical energy to a transducer for sealing a vessel, wherein a frequency of the electrical energy is in an ultrasound range;

controlling the electrical energy to achieve a predetermined velocity of an end effector coupled to the transducer, when the end effector is grasping the vessel;
sensing parameters of the electrical energy;
calculating power of the electrical energy based on the sensed parameters, when the end effector achieves the predetermined velocity with the power;
estimating a size range of the vessel based on the power; and
controlling the electrical energy to achieve a target velocity, which is determined based on the estimated size range of the vessel, to seal the vessel.

2. The method according to claim 1, wherein the size range of the vessel is greater than or equal to 5 mm when the power is greater than or equal to a predetermined power threshold.

3. The method according to claim 1, wherein the size range of the vessel is less than 5 mm when the power is less than a predetermined power threshold.

4. The method according to claim 1, wherein controlling the electrical energy based on the estimated size range of the vessel includes controlling power of the electrical energy to seal the vessel based on the estimated size range of the vessel.

5. The method according to claim 1, wherein the power is calculated by subtracting power losses in the transducer and a waveguide in the ultrasonic surgical device from the power of the electrical energy.

6. The method according to claim 1, wherein the power is calculated about 100 milliseconds after providing the electrical energy.

7. The method according to claim 1, wherein controlling the electrical energy based on the estimated size range of the vessel to seal the vessel includes:
determining whether the power is in a first range or in a second range, which is at least partially higher than the first range; and
setting a first target velocity when the power is determined to be in the first range, and a second target velocity when the power is determined to be in the second range.

8. The method according to claim 7, wherein controlling the electrical energy based on the estimated size range of the vessel to seal the vessel further includes:
controlling the electrical energy to maintain the first or second target velocity of the end effector to seal the vessel.

9. The method according to claim 7, wherein the first target velocity is greater than the predetermined velocity.

10. The method according to claim 7, wherein the second target velocity is less than the predetermined velocity.

11. An ultrasonic surgical device comprising:
a transducer;
an end effector coupled to the transducer and configured to grasp and seal a vessel;
a power source configured to supply electrical energy to the transducer;
a sensor configured to sense parameters of the electrical energy; and
a controller configured to:
control the electrical energy to achieve a predetermined velocity of the end effector coupled to the transducer, when the end effector is grasping the vessel;
calculate power of the electrical energy based on the sensed parameters, when the end effector achieves the predetermined velocity with the power;
estimate a size range of the vessel based on the power; and
control the electrical energy to achieve a target velocity, which is determined based on the estimated size range of the vessel, to seal the vessel.

12. The ultrasonic surgical device according to claim 11, wherein the size range of the vessel is estimated to be greater than or equal to 5 mm when the power is greater than or equal to a predetermined power threshold.

13. The ultrasonic surgical device according to claim 11, wherein the size range of the vessel is estimated to be less than 5 mm when the power is less than a predetermined power threshold.

14. The ultrasonic surgical device according to claim 11, wherein the controller is further configured to control power of the electrical energy to seal the vessel based on the estimated size range of the vessel.

15. The ultrasonic surgical device according to claim 11, wherein the power is calculated by subtracting power losses in the transducer and a waveguide in the ultrasonic surgical device from the power of the electrical energy.

16. The ultrasonic surgical device according to claim 11, wherein the power is calculated about 100 milliseconds after providing the electrical energy.

17. The ultrasonic surgical device according to claim 11, wherein the controller is further configured to:
determine whether the power is in a first range or in a second range, which is at least partially higher than the first range; and
set a first target velocity when the power is determined to be in the first range, and a second target velocity when the power is determined to be in the second range.

18. The ultrasonic surgical device according to claim 17, wherein the controller is further configured to control the electrical energy to maintain the first or second target velocity of the end effector to seal the vessel.

19. The ultrasonic surgical device according to claim 17, wherein the first target velocity is greater than the predetermined velocity.

20. The ultrasonic surgical device according to claim 17, wherein the second target velocity is less than the predetermined velocity.

* * * * *